United States Patent [19]

Lam

[11] 4,071,321
[45] Jan. 31, 1978

[54] TEST COMPOSITION AND DEVICE FOR DETERMINING PEROXIDATIVELY ACTIVE SUBSTANCES

[75] Inventor: Charles Tak Wai Lam, Elkhart, Ind.

[73] Assignee: Miles Laboratories, Inc., Elkhart, Ind.

[21] Appl. No.: 777,001

[22] Filed: Mar. 14, 1977

[51] Int. Cl.² .................... G01N 31/22; G01N 33/16
[52] U.S. Cl. ........................ 23/253 TP; 23/230 B; 252/408
[58] Field of Search ................. 23/253 TP, 230 B; 252/408

[56] References Cited

U.S. PATENT DOCUMENTS

| 3,012,976 | 12/1961 | Adams, Jr. et al. | 23/230 B X |
|---|---|---|---|
| 3,252,762 | 5/1966 | Adams, Jr. et al. | 23/253 TP |
| 3,853,470 | 12/1974 | Morin et al. | 252/408 X |
| 3,853,471 | 12/1974 | Rittersdorf et al. | 23/253 TP |
| 3,917,452 | 11/1975 | Rittersdorf et al. | 23/230 B |
| 4,017,261 | 4/1977 | Svoboda et al. | 252/408 X |

*Primary Examiner*—Robert M. Reese
*Attorney, Agent, or Firm*—E. H. Gorman

[57] ABSTRACT

A test composition, device, and method for determining the presence of a peroxidatively active substance in a sample are disclosed. The composition comprises
 a. an organic hydroperoxide,
 b. an indicator capable of producing a detectable response in the presence of a hydroperoxide and a peroxidatively active substance,
 c. a diluent compound having the structure

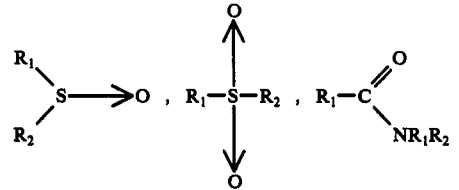

or mixtures thereof, in which $R_1$ and $R_2$, same or different, are hydrogen, alkyl or alkoxy having 1 to about 6 carbon atoms, or aryl, and
 d. a borate ester having the structure

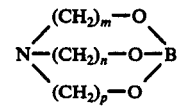

in which $m$, $n$ and $p$, same or different, are integers of 1 to about 4.

The device comprises a carrier matrix incorporated with the composition, and the method comprises contacting a sample, suspected of containing a peroxidatively active substance, with said composition.

63 Claims, No Drawings

TEST COMPOSITION AND DEVICE FOR DETERMINING PEROXIDATIVELY ACTIVE SUBSTANCES

BACKGROUND OF THE INVENTION

1. Field of the Invention

The present invention relates to the detection of constituents in a test sample. More particularly, the invention relates to the qualitative and semi-quantitative analysis of a sample for constituents which possess peroxidative activity.

2. Description of the Prior Art

Many analytical methods are presently available for detecting the presence of a peroxidatively active substances in samples such as urine, fecal suspensions, and gastrointestinal contents. Hemoglobin and its derivatives are typical of such "peroxidatively active" substances because they behave in a manner similar to the behavior of the enzyme peroxidase. Such substances have also been referred to as pseudoperoxidases. Peroxidatively active substances are enzyme-like in that they catalyze the redox reaction between peroxides and benzidine, o-tolidine, 3,3′,5,5′-tetramethylbenzidine, 2,7-diaminofluorene or similar indicator substances, thereby producing a detectable response such as a color change. Hence, most methods for determining the presence of occult blood in test samples rely on this pseudoperoxidase activity.

Several methods have evolved over the years which rely on enzyme-like catalysis of the peroxidic oxidation of color-forming indicators. Primarily these include wet chemical procedures and "dip-and-read" type reagent-bearing strips. Of the former, a typcial example is set forth in Richard M. Henry, et al., *Clinical Chemistry Principles and Techniques* (Hagerstown, Maryland: Harper and Row, 1974), pp. 1124–1125. The procedure involves the use of glacial acetic acid (buffer), diphenylamine (indicator), and hydrogen peroxide. While such wet methods have proven analytical ability, they are nevertheless fraught with obvious shortcomings, not the least of which are poor reagent stability and inadequate sensitivity. Inherent to such reagent solutions is a decline in stability (ergo sensitivity) so rapid that fresh reagent solutions must be prepared after several days of storage, a necessity resulting in both excessive time required of analytical personnel, and poor economy because of having to waste costly reagents.

A second method for the determination of peroxidatively active substances, and the one presently preferred by clinical assayists and analysts, is the use of so-called "dip-and-read" reagent strips. Typical of such devices is a reagent strip manufactured by the Ames Company Division of Miles Laboratories, Inc. and sold under the name HEMASTIX ®. This reagent strip comprises, in essence, a porous paper matrix affixed to a plastic strip or handle. The paper is impregnated with a buffered mixture of an organic hydroperoxide and o-tolidine. Upon immersion in a liquid containing hemoglobin, myoglobin, erythrocytes or other pseudoperoxidases, a blue color develops in the paper, the intensity of which is proportional to the concentration of the peroxidatively active substance in the sample. Thus, by comparing the color developed in the reagent strip to a standard color chart, the assayist can determine, on a semi-quantitative basis, the amount of unknown present in the sample.

Hence, the advantages of reagent strips over wet chemistry methods are predominantly twofold: strips are easier to use because neither the preparation of reagents nor the attendant apparatus are required; and greater stability of regents is afforded, resulting in greater accuracy, sensitivity and economy.

But the inherent advantages of strips over wet chemistry notwithstanding, the characteristics of stability and sensitivity are in need of still further improvement. Whereas these properties in current state-of-the-art strips for determining pseudoperoxidases are greatly enhanced over those of wet chemical methods, there would nevertheless accrue a great advance in the art if such strips could be made even more stable during storage and even more sensitive to peroxidatively active substances. It was towards achieving these improvements that the research activities resulting in the present invention were directed.

At least three attempts at achieving the above-mentioned goals are recorded in the prior art. A recitation in *Chemical Abstracts* Volume 85, page 186 (1976) describes a two-dip method for preparing reagent strips containing o-tolidine and phenylisopropyl hydroperoxide. In this method a solution is made of the indicator (o-tolidine · 2HCl) and polyvinylpyrrolidone in ethanol. To this solution were added a small amount of surfactant and enough citrate buffer to provide a pH of 3.7. Filter paper strips impregnated with ethyl cellulose were dipped in this solution and dried. The thus-impregnated filter paper was subsequently dipped into a second solution containing 1,4-diazabicyclo [2.2.2]octane, phenylisopropyl hydroperoxide and polyvinylpyrrolidone dissolved in an ethanol-toluene mixture. The thrust of this experiment was to stabilize the peroxide and indicator combination through the use of the bicyclooctane derivative and the polyvinylpyrrolidone.

A second such method is disclosed in U.S. Pat. No. 3,853,471. This patent teaches the use of phosphoric or phosphonic acid amides where the substituent amido groups are primarily N-morpholine radicals.

Besides these attempts, there also exists the disclosure of U.S. Pat. No. 3,252,762 wherein the organic hydroperoxide is physically encapsulated within a colloidal material such as gelatin. Thus, when such a test strip is utilized, the aqueous test sample dissolves the gelatin capsules, thereby freeing the hydroperoxide for further reaction with the indiactor in the presence of a peroxidatively active substance.

Each of these prior attempts was aimed at stabilizing the reagents so that the potentially incompatible reactive ingredients (hydroperoxide and indicator) would not prematurely combine and thereby render the test strips less sensitive. Hence, it can be said that the prior art methods were not directed towards the combined objectives of simultaneously enhancing stability and sensitivity, but rather they attempted to preserve existing sensitivity by preventing reagent decomposition during storage.

Another prior art reference which is of interest in U.S. Pat. No. 3,236,850. This patent is directed towards stabilizing organic hydroperoxides used as catalysts and oxidizing agents. The patentees in this reference disclose the use of primary, secondary, or tertiary amine salts with organic peroxides. This reference is in no way directed toward reagent test strips.

Upon realizing that none of the above-described methods would achieve the kind of stability and sensitivity desired in a test strip for detecting peroxidatively active substances, the present inventor decided to take a completely different tack. This different approach was discovered during the research which led to the present invention, and resulted in a composition and device which completely fulfilled the desired objectives of increased stability and sensitivity.

But, even more surprisingly, yet another advantage resulted from this work - an improved method for preparing the device presently disclosed whereby the manufacture is dramatically simpler than processes enumerated in the foregoing prior art references - a one-dip method.

SUMMARY OF THE INVENTION

Briefly stated, the present invention relates to a test composition and device for determining the presence of a pseudoperoxidase in a test sample. The test composition comprises (i) an organic hydroperoxide; (ii) an indicator capable of producing a detectable response in the presence of a hydroperoxide and a peroxidatively active substance; (iii) a diluent having the structure

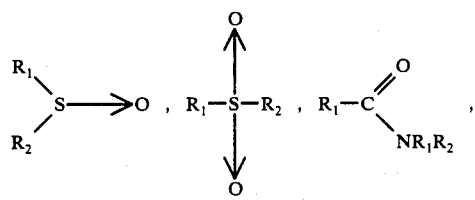

or mixtures thereof, in which $R_1$ and $R_2$, same or different, are alkyl or alkoxy having 1 to about 6 carbon atoms, or aryl; and (iv) a borate ester having the structure

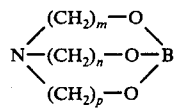

in which $m$, $n$ and $p$, same or different, are integers of 1 to about 4.

The device of the present invention comprises the above composition incorporated with a carrier matrix. The process comprises the steps of preparing the test composition and incorporating it with the matrix.

DETAILED DESCRIPTION OF THE INVENTION

The organic hydroperoxide contemplated for use in the test composition can be selected from many well-known organic hydroperoxides. It must, however, be capable of reacting with a peroxidatively-sensitive indicator to produce a detectable response such as a color change or change in the amount of light absorbed or reflected by the test composition. Among hydroperoxides which have been found suitable are t-butyl hydroperoxide, cumene hydroperoxide, diisopropylbenzene hydroperoxide, 2,5-dimethylhexane-2,5-dihydroperoxide, paramenthane hydroperoxide or mixtures thereof. Of these, cumene hydroperoxide has been found to be most preferable.

There exist many indicators which are capable of producing a detectable response in the presence of a hydroperoxide and a pseudoperoxidase, and which are, therefore, suitable for use in the present invention. These include the so-called "benzidine-type" compounds, typical of which are benzidine, o-tolidine, 3,3',5,5'-tetramethylbenzidine, 2,7-diaminofluorene or mixtures of these in varying proportions.

The borate esters which are presently believed to contribute to the increased stability and sensitivity of the present invention have the structure depicted above. Of the compounds included in this generic structure, it has been found that trimethanolamine borate, triethanolamine borate and tri(n-propanol)amine borate are particularly suitable. These compounds correspond to the above generic formula where $m$, $n$ and $p$ are the same integer and are 1, 2, and 3, respectively.

The amount of the borate ester useful in the present composition and device can vary broadly. This is reflected in the Examples, infra. Thus, in Example I the molar ratio of triethanolamine borate equivalents to cumene hydroperoxide equivalents is 4.71. Conversely, Example III evidences a 2.83 molar ratio of borate to hydroperoxide (1.42 normality ratio if the difunctionality of the peroxide is considered).

But the equivalents ratio range of about 1.4 to about 5, as shown in the Examples, is by no means limiting with respect to the amount of borate useful in the present invention. Any amount sufficient to achieve the desired degree of test composition stability and sensitivity can be employed, and this amount is easily determinable at the laboratory bench, given the present invention disclosure.

The test composition is typically prepared by dissolving or suspending portions of each ingredient in water or other suitable suspending medium or solvent. Other suitable solvents include chloroform, methanol, ethanol, methylene chloride, cyclohexane, etc.

In a preferred embodiment of the present invention, the composition comprises cumene hydroperoxide, o-tolidine, a mixture of dimethyl sulfone and dimethyl sulfoxide, and triethanolamine borate.

The test device can be prepared from a one-dip process. Accordingly, a portion of carrier matrix material is immersed in the solution or suspension and subsequently dried. Test devices thus prepared exhibit little loss in reactivity even after storage under stress conditions such as about 60° to about 70° C for 1 to 3 days and longer. By way of comparison, test devices were similarily prepared, but without the presence of the borate ester or the diluent. When these strips were stored under substantially identical stress conditions, a dramatic loss in reactivity and sensitivity was observed.

The carrier matrix utilized in forming the test device can take on a multitude of forms. Thus, U.S. Pat. No. 3,846,247 teaches the use of felt, porous ceramic strips, and woven or matted glass fibers. Additionally, U.S. Pat. No. 3,552,928 teaches the use of wood sticks, cloth, sponge material, and argillaceous substances. The use of synthetic resin fleeces and glass fiber felts as a carrier matrix is suggested in British Pat. No. 1,369,139. Another British Pat. No. 1,349,623, proposes the use of light-permeable meshwork of thin filaments as a cover for an underlying paper matrix. Polyamide fibers are taught in French Pat. No. 2,170,397. These suggestions notwithstanding, however, the material predominantly used in the art as a carrier matrix, and that which is especially suitable for the present invention, is a bibulous paper such as filter paper. It can thus be seen that there is a great deal of leeway in selecting an appropriate material for use as a carrier matrix, and the matrix can take on various physical forms. All of these types are intended as being within the scope of the present invention.

The mechanism whereby the present approach to enhanced stability and sensitivity is realized is not known with certainty. However the unique chemical characteristics of the borate ester described and claimed in the instant invention give rise to reasonable grounds for speculation. It is known that peroxides are generally unstable compounds, or at least less stable than most compounds occurring in nature. Some are explosive. Others, such as organic hydroperoxides (viz. cumene hydroperoxide) are relatively stable, but are believed to easily dissociate in the presence of acids such as those commonly employed in occult blood-sensitive test devices. When this decomposition occurs in the presence of an oxidizable indicator (such as those described herein) a redox reaction takes place. It is believed that this premature interaction is the cause of decreased sensitivity in peroxidatively sensitive reagent strips.

On the other hand, borate esters such as those described herein are unique in the geometry of the nitrogen and boron atoms in the bicyclic structure, each comprising a separate bridgehead atom. The nitrogen atom at one bridgehead is electron-rich, containing an unshared pair of electrons projecting outwards from the molecular axis. The other bridgehead atom, the boron atom, situated at the other axial end of the molecule, is electron deficient and tends to coordinately bond with electron-rich anions.

Hence, because of its electron richness, the nitrogen end of the molecule could quite conceivably tie up a proton, whereas the electron-deficient boron bridgehead atom could coordinately couple with an anionic peroxide residue. Thus, it is believed that the unique electron distribution in the presently discussed bicylic molecules stabilizes the organic peroxide in the present test composition by chemically inserting itself between the peroxidic proton and oxygen atom, forming a coordinately coupled ion pair.

Thus, in the present test composition, the surprisingly increased stability is believed to arise from the organic hydroperoxide being precluded from ionically interacting with the indicator until the solvating power of the test sample destroys the peroxide-borate complex, and frees the peroixde to oxidize the indicator in the presence of a peroxidatively active substance.

But even though marked increases in stability and sensitivity result from the use of borate esters, it has surprisingly been found that even greater stability and sensitivity ensue when the borate ester and the above-described diluent are both included in the test composition.

The diluent compounds which are presently believed to contribute to the increased stability and sensitivity of the present invention have the structures depicted above. Of the compounds included in these generic structures, it has been found that N,N-dimethyl formamide, dimethyl sulfoxide, dimethyl sulfone, or their mixtures are especially suitable. Other diluents found to be operable are benzyl sulfoxide, 4-chlorophenyl sulfone, 4-fluoro-3-nitrophenyl sulfone and others. These compounds correspond to the above structural formulas where $R_1$ and $R_2$ are each methyl.

The scope of $R_1$ and $R_2$ encompassed by the presently dislcosed inventive concepts is broad. Hence, by $R_1$ and $R_2$ are meant substituted or unsubstituted alkyl of 1 to about 6 carbon atoms. Illustrative of alkyl groups are methyl, ethyl, propyl, isopropyl, n-butyl, isobutyl, sec-butyl, n-pentyl, isopentyl, neopentyl, t-pentyl and other isomers, including those of hexane. These alkyl groups are also illustrative of the alkoxy groups intended as satisfying the foregong definition of $R_1$ and $R_2$.

When $R_1$ and $R_2$ are aryl, the scope is likewise broad and the term aryl, as used herein, includes substituted and unsubstituted aryl groups such as phenyl, benzyl tolyl, anilino, naphthyl, etc.

Typical of groups with which $R_1$ and $R_2$ may be substituted are amino, nitro, amido, nitrilo, hydroxyl, alkyloxy, halogen, phenyl, sulfonic acid, carboxylic acid, etc.

The amount of diluent utilized in the presently disclosed composition, device and process can vary widely, and can easily be determined at the laboratory bench. Thus, when the diluent is a liquid such as dimethyl sulfoxide, (see Table II, infra) the amount can vary from about 10% to about 100% based on the volume of diluent added to the composition, compared with the volume of solvent or suspending agent (in the case of Example XII, water). A preferred range is about 25% to about 100%.

Likewise, when the diluent is a mixture of more than one of the diluent compounds disclosed herein, the ratio of the amounts of the several compounds used in the diluent can vary broadly, and these, also, can readily be determined in the laboratory.

In order to more clearly teach how to make and use the present invention, and to illustrate presently preferred embodiments thereof, the following examples are provided.

A. PREPARATION OF THE TEST COMPOSITION AND DEVICE

EXAMPLE I — THE TEST COMPOSITION

A test composition was prepared by dissolving the following ingredients in 150 ml (milliliters) of deonized water. The ingredients were added to the water in descending order as listed.

| | |
|---|---|
| Trisodium citrate | 3.2 g (grams) |
| Citric Acid | 2.2 g |
| Ethylenediaminetetraacetic acid, tetrasodium salt | 0.1 g |
| Dimethylsulfone | 10.0 g |
| Sodium lauryl sulfate | 1.0 g |
| 6-Methoxyquinoline | 0.5 g |
| Dimethylsulfoxide | 25.0 ml (milliliters) |
| Acetone | 25.0 ml |
| Cumene hydroperoxide | 2.0 g |
| Triethanolamine borate (Aldrich Chemical Co., Inc.) | 10.0 g |
| o-tolidine | 0.4 g |

EXAMPLE II — THE TEST DEVICE

Strips of Whatmann 3MM filter paper were immersed in the test composition of Example I. The immersed strips were dried at 70° C for about 15 minutes to form test composition-impregnated carrier matrices. The dried carrier matrices were then attached to plastic (polystyrene) strips or handles by means of double-faced adhesive tape purchased from 3M Company. The resulting test devices can be used to detect peroxidatively active substances by immersion in a test sample, such as urine, suspected of containing such substance, and observing any development of color in the carrier matrix.

B. STABILITY TESTING OF VARIOUS TEST COMPOSITIONS

EXAMPLE III — THE EFFECT OF THE BORATE ESTER

The purpose of this experiment was to demonstrate the effect of triethanolamine borate on occult blood test compositions as compared with other known additives. The following solution was prepared.

| | | |
|---|---|---|
| chloroform | 100 | ml |
| o-tolidine | 0.5 | g |
| 2,5-dimethylhexane-2,5-dihydroperoxide | 2.0 | g |
| poly(N-vinylpyrrolidone) | 10.0 | g |

To aliquot portions of this solution (20 ml each) were added 1 gram of the additives in the following table. These test composition solutions were permitted to stand at room temperature for about 5 hours and the results observed are tabulated below in Table I.

TABLE I

| SAMPLE NO. | ADDITIVE | RESULTS |
|---|---|---|
| 1 | hexamethylenetetramine | Very dark, almost black solution. Poor sensitivity. |
| 2 | 1,4-diazabicyclo-[2.2.2]octane | Dark green/brown discoloration. Minimally sensitive to occult blood in urine. |
| 3 | triethanolamine borate | Slight browing. High sensitivity to occult blood in urine |
| 4 | control (no additive) | Turned black in about 2 hours. Unusable in occult blood analysis. |

EXAMPLE IV — THE EFFECT OF THE DILUENT

To a 500 ml beaker were added the following components:

| | | |
|---|---|---|
| chloroform | 100 | ml |
| cumene hydroperoxide | 4.0 | g (grams) |
| o-tolidine | 0.4 | g |
| dimethyl sulfoxide | 25.0 | ml |

The resultant test composition, which was slightly yellow upon combining the above ingredients, was transferred to an Erlenmeyer flask which was stoppered and left on the laboratory bench at room temperature (about 18.3° C) overnight. After one day the test composition had grown only slightly darker than when it was prepared.

EXAMPLE V — COMPARISON WITH EXAMPLE IV

A test composition for control purposes, i.e., for comparison with the present invention, was prepared by following the procedure of Example IV, except that the dimethyl sulfoxide was substituted by 25 ml additional chloroform. This test composition, without dimethyl sulfoxide, was stoppered in an Erlenmeyer flask and left on the laboratory bench as in Example IV (i.e., at 18.3° C for 1 day). Contrary to the composition of Example IV, the control composition darkened to almost black, thus indicating the improved stability imparted to the test composition by the diluent.

C. THE STABILIZATION OF TEST DEVICES BY THE BORATE ESTER

EXAMPLE VI — CONTROL

A solution of the following test composition was prepared for preparation of a reagent strip sensitive to pseudoperoxidases. This formulation does not contain the borate ester component of the present invention.

| | | |
|---|---|---|
| H₂O | 150 | ml |
| Trisodium Citrate | 3.2 | g |
| Citric Acid | 2.2 | g |
| Ethylenediaminetetraacetic acid, tetrasodium salt | 0.1 | g |
| Dimethylsulfone | 10.0 | g |
| Sodium lauryl sulfate | 1.0 | g |
| 6-methoxyquinoline | 0.5 | g |
| Dimethylsulfoxide | 25.0 | ml |
| Acetone | 25.0 | ml |
| Cumene hydroperoxide | 2.0 | g |
| o-tolidine | 0.4 | g |

A section of Whatmann 3MM filter paper was immersed in the above test composition solution and dried at 70° C. The dried paper was cut into squares of about 5 mm, and these were attached to plastic handles using double-faced adhesive tape (available from 3M Company) thereby forming test devices.

EXAMPLE VII — PRESENT INVENTION

A solution was prepared as in Example VI, above, except that 10g triethanolamine borate was added prior to the addition of the cumene hydroperoxide. Test devices were prepared from this solution in identical fashion as in Example VI.

EXAMPLE VIII — 1,4-DIAZABICYCLO [2.2.2]OCTANE

A solution was prepared as in Example VI, supra, except that 10g 1,4-diazabicyclo[2.2.2]octane was added prior to the addition of cumene hydroperoxide. This solution was used to prepare test devices in identical fashion as in Example VI.

EXAMPLE IX — HEXAMETHYLENETETRAMINE

A solution was prepared as in Example VI, supra, except that 10g hexamethylenetetramine was added prior to the addition of cumene hydroperoxide. Test devices were prepared from this solution as in Example VI, supra.

EXAMPLE X — STABILITY AND SENSITIVITY COMPARISON

The test devices of Examples VI - IX were placed under stressed conditions to determine their relative stabilities and sensitivities. Devices from Examples VI - VIII were stored for three days at about 60° C, and those of Example IX for one day at about 70° C. These stressed test devices were then tested for sensitivity by immersion in urine containing one part per million blood. Only the device containing triethanolamine borate (Example VII) produced a change in color at this occult blood concentration (viz., 0.015 milligrams per deciliter). The remaining devices were insensitive to this level of occult blood.

D. THE STABILIZATION OF TEST DEVICES BY THE DILUENT

EXAMPLE XI

Six test devices were prepared from six test composition solutions containing varying amounts of dimethyl sulfoxide in accordance with Table II below.

The six test composition solutions were all prepared with the following formula:

| | | |
|---|---|---|
| water | 75 | ml |
| trisodium citrate | 3.2 | g |
| citric acid | 4.5 | g |
| triethanolamine borate | 10.0 | g |
| ethylenediamine tetra-acetic acid, tetrasodium salt | 0.1 | g |
| dimethyl sulfone | 5.0 | g |
| sodium lauryl sulfate | 1.0 | g |
| 6-methoxyquinoline | 0.5 | g |
| cumene hydroperoxide | 2.0 | g |
| o-tolidine | 0.4 | g |

To each of the six test composition solutions were added, respectively, the following amounts of dimethyl sulfoxide and methanol:

TABLE II

| Test Composition NO. | Dimethyl sulfoxide (ml) | Methanol (ml) |
|---|---|---|
| 1 | 0 | 75 |
| 2 | 5 | 70 |
| 3 | 10 | 65 |
| 4 | 25 | 50 |
| 5 | 40 | 35 |
| 6 | 60 | 15 |

Test devices were then prepared from each of the above test composition solutions by immersing a piece of Whatmann 3MM filter paper into each solution. The immersed strips of filter paper were withdrawn from their respective solutions, and dried and stressed in an oven at 70° C for 18 hours.

After stressing, each strip was tested in a test solution comprising a 1:1,000,000 dilution of fresh whole blood in urine. The intensity of color developing in each strip provided a comparison means. The results are tabulated in Table III.

Table III

| Test Device No.* | Color Rating** |
|---|---|
| 1 | 0 (no color) |
| 2 | 1 (trace) |
| 3 | 3 |
| 4 | 5 |
| 5 | 6 |
| 6 | 7 (almost no loss in reactivity) |

*Test device numbers corespond to the test composition numbers in Table II.
**The color rating was based on a scale of 0 to 8, 8 being the color produced by a freshly prepared, unstressed test device prepared from test composition no. 6 (Table II). A rating of 0 indicates no color formation, a rating of 7 indicates almost no loss of reactivity, and a rating of 1 indicates only trace amounts of color.

It is dramatically apparent from the data in Table III, that sensitivity increases with the amount of diluent (here, dimethyl sulfoxide) used in the test composition formulation.

E. INCREASED STABILITY OF THE TEST COMPOSITION (WITH BORATE ESTER) IMPARTED BY VARIOUS DILUENTS

EXAMPLE XII

Eight test compositions were prepared as in Example XI, 7 of which contained different diluents and one (control) having no diluent. The purpose of this experiment was to assess the efficacy of various diluents in increasing the stability of test compositions sensitive to peroxidatively active substances where the amount of borate ester in the composition is held constant.

A solution was prepared containing the following ingredients:

| | | |
|---|---|---|
| water | 50 | ml |
| trisodium citrate | 3.2 | g |
| citric acid | 2.2 | g |
| sodium lauryl sulfate | 1.0 | g |
| 6-methoxyquinoline | 1.0 | g |
| methanol | 50.0 | ml |
| triethanolamine borate | 5.0 | g |
| cumene hydroperoxide | 2.0 | g |
| o-tolidine | 0.4 | g |

A small aliquot of this solution was added to each of 8 test tubes. Thereafter small amounts of the diluents listed in Table IV were added to each test tube, the test tubes stoppered, and allowed to stand at room temperature on the laboratory bench for one week. At the end of the week, the test tubes were examined for relative darkening in color, the darker the color, the less stable the test composition. The results are given in Table IV in order of decreasing stability (i.e., test composition 1 being most stable and test composition 8 being least stable).

TABLE IV

| Test Composition No. | Diluent |
|---|---|
| 1 | dimethyl sulfoxide |
| 2 | N,N-dimethyl formamide |
| 3 | dimethyl sulfone |
| 4 | benzyl sulfoxide |
| 5 | 4-chlorophenyl sulfone |
| 6 | 4-fluoro-3-nitrophenyl sulfone |
| 7 | 2-imidazolidone |
| 8 (control) | none |

In Table IV, samples 1 and 2 exhibited excellent stability; solution 3 less so, but nevertheless having good stability; solutions 4-7 were moderately stable; and solution 8, the control, was far less stable than solutions 1-7.

F. PREFERRED EMBODIMENTS

EXAMPLE XIII

The following ingredients are mixed in 150 ml water:

| | | |
|---|---|---|
| Trisodium citrate | 3.2 | g |
| Citric Acid | 2.2 | g |
| Ethylenediaminetetraacetic acid, tetrasodium salt | 0.1 | g |
| Dimethyl sulfone | 10.0 | g |
| Sodium lauryl sulfate | 1.0 | g |
| 6-methoxyquinoline | 0.5 | g |
| Dimethylsulfoxide | 25.0 | ml |

| -continued | | |
|---|---|---|
| Acetone | 25.0 | ml |
| Triethanolamine borate | 10.0 | g |
| cumene hydroperoxide | 2.0 | g |
| o-tolidine | 0.4 | g |

Strips of Whatmann 3MM filter paper were immersed in the above solution and dried at 70° C. When dried, the filter paper was cut into squares measuring 4 mm on a side. These squares were then mounted on polystyrene handles measuring about 8 × 15 mm, by use of double-faced adhesive tape (3M Company).

Test devices prepared in accordance with the above experiment were stressed at 60° C for 3 days and were found sensitive to occult blood in urine at concentrations at least as low as 0.015 milligram percent.

EXAMPLE XIV

This example illustrates a second preferred embodiment of the presently disclosed test device.

A test composition is prepared by mixing the following ingredients, in the following order, in a beaker with stirring:

| water | 75 | ml |
|---|---|---|
| trisodium citrate | 3.2 | g |
| citric acid | 4.15 | g |
| triethanolamine borate | 10.0 | g |
| ethylenediaminetetraacetic acid | 0.1 | g |
| sodium lauryl sulfate | 1.5 | g |
| dimethyl sulfone | 10.0 | g |
| 6-methoxyquinoline | 0.6 | g |
| N,N-dimethyl formamide | 75 | ml |
| cumene hydroperoxide | 3.0 | g |
| o-tolidine | 0.8 | g |

Strips of Whatmann 3MM filter paper were immersed in the above composition and dried from about 11 minutes at about 90° to 92° C. The dried strips were then mounted on plastic handles using double adhesive tape.

Some of the strips were stressed by storage at 70° C. for 1 day; others by storing at 40° C for 12 weeks. Both sets of strips developed a blue/green color when contacted by a 1:1 × 10⁶ dilution of fresh whole blood in urine.

In summary, the preceding Examples point out how to make and use the composition and test device of the present invention (Examples I and II), present comparative results of stability and sensitivity (Examples III to XII), and describe presently preferred embodiments (Examples XIII and XIV). The effects of the borate ester and the diluent, both singly and in concert, on the test composition are portrayed in Examples III to V, whereas the effects on the test device are shown in Examples VI to XI. The use of various diluents is embodied in Example XII.

What is claimed is:

1. A one-dip process for preparing a test device for determining the presence of a peroxidatively active substance in a test sample, said process comprising the steps of
   a. preparing a test composition by combining (i) an organic hydroperoxide, (ii) an indicator capable of producing a detectable response in the presence of said hydroperoxide and a peroxidatively active substance, (iii) a diluent having the structure

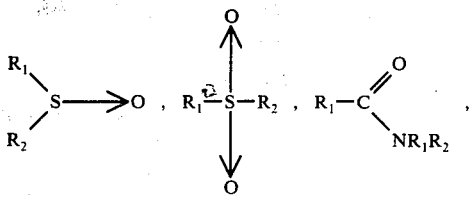

or mixtures thereof, in which
$R_1$ and $R_2$, same or different, are hydrogen, alkyl or alkoxy having 1 to about 6 carbon atoms, or aryl, and
(iv) a borate ester having the structure

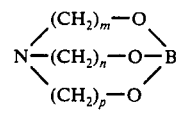

in which $m$, $n$ and $p$, same or different, are integers of 1 to about 4; and
   b. incorporating said test composition with a carrier matrix.

2. The process of claim 1 in which the diluent is dimethyl sulfoxide, dimethyl sulfone, N,N-dimethyl formamide, benzyl sulfoxide, 4-chlorophenyl sulfone, 4-fluoro-3-nitrophenyl sulfone or mixtures thereof.

3. The process of claim 1 in which the diluent is a mixture of dimethyl sulfone and N,N-dimethyl formamide.

4. The process of claim 1 in which the borate ester is trimethanolamine borate, triethanolamine borate, tri(n-propanol)amine borate or mixtures thereof.

5. The process of claim 1 in which the borate ester is triethanolamine borate.

6. The process of claim 1 in which the diluent is dimethyl sulfoxide, dimethyl sulfone, N,N-dimethyl formamide or mixtures thereof, and the borate ester is trimethanolamine borate, triethanolamine borate, tri(n-propanol)amine borate or mixtures thereof.

7. The process of claim 1 in which the diluent is a mixture of dimethyl sulfone and N,N-dimethyl formamide, and the borate ester is triethanolamine borate.

8. The process of claim 1 in which the organic hydroperoxide is t-butyl hydroperoxide, cumene hydroperoxide, diisopropylbenzene hydroperoxide, 2,5-dimethylhexane-2,5-dihydroperoxide, paramenthane hydroperoxide or mixtures thereof.

9. The process of claim 1 in which the organic hydroperoxide is cumene hydroperoxide.

10. The process of claim 1 in which the indicator is benzidine, o-tolidine, 3,3′,5,5′-tetramethylbenzidine, 2,7-diaminofluorene, or mixtures thereof.

11. The process of claim 1 in which the indicator is o-tolidine.

12. A test device for determining the presence of a peroxidatively active substance in a test sample, said device being prepared by the process of claim 1.

13. The test device of claim 12 in which the diluent is dimethyl sulfoxide, dimethyl sulfone, N,N-dimethyl formamide, benzyl sulfoxide, 4-chlorophenyl sulfone, 4-fluoro-3-nitrophenyl sulfone or mixtures thereof.

14. The test device of claim 12 in which the diluent is a mixture of dimethyl sulfone and N,N-dimethyl formamide.

15. The test device of claim 12 in which the borate ester is trimethanolamine borate, triethanolamine borate, tri(n-propanol)amine borate or mixtures thereof.

16. The test device of claim 12 in which the borate ester is triethanolamine borate.

17. The test device of claim 12 in which the diluent is dimethylsulfoxide, dimethyl sulfone, N,N-dimethyl formamide or mixtures thereof, and the borate ester is trimethanolamine borate, triethanolamine borate, tri(n-propanol)amine borate or mixtures thereof.

18. The test device of claim 12 in which the diluent is a mixture of dimethyl sulfone and N,N-dimethyl formamide, and the borate ester is triethanolamine borate.

19. The test device of claim 12 in which the organic hydroperoxide is t-butyl hydroperoxide, cumene hydroperoxide, diisopropylbenzene hydroperoxide, 2,5-dimethylhexane-2,5-dihydroperoxide, paramenthane hydroperoxide or mixtures thereof.

20. The test device of claim 12 in which the organic hydroperoxide is cumene hydroperoxide.

21. The test device of claim 12 in which the indicator is benzidine, o-tolidine, 3,3',5,5'-tetramethylbenzidine, 2,7-diaminofluorene, or mixtures thereof.

22. The test device of claim 12 in which the indicator is o-tolidine.

23. A one-dip process for preparing a test device for determining the presence of a peroxidatively active substance in a test sample, said process comprising the steps of
   a. preparing a test composition comprising cumene hydroperoxide, o-tolidine, a mixture of dimethyl sulfone and N,N-dimethyl formamide, and triethanolamine borate; and
   b. incorporating said composition with a carrier matrix.

24. The process of claim 23 in which the carrier matrix is bibulous paper.

25. A test device for determining the presence of a peroxidatively active substance in a test sample, said device being prepared by the process of claim 23.

26. The test device of claim 25 in which said carrier matrix is bibulous paper.

27. A test composition for determining the presence of a peroxidatively active substance in a test sample, said composition comprising
   a. an organic hydroperoxide,
   b. an indicator capable of producing a detectable response in the presence of said hydroperoxide and a peroxidatively active substance,
   c. a diluent having the structure

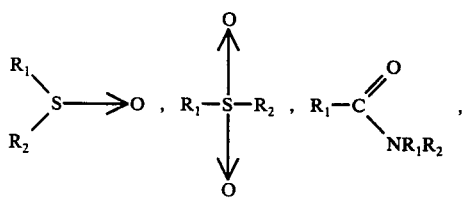

or mixtures thereof, in which
$R_1$ and $R_2$, same or different, are hydrogen, alkyl or alkoxy having 1 to about 6 carbon atoms, or aryl, and
   d. a borate ester having the structure

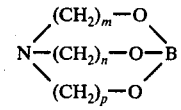

in which $m$, $n$ and $p$, same or different, are integers of 1 to about 4.

28. The composition of claim 27 in which the diluent is dimethyl sulfoxide, dimethyl sulfone, N,N-dimethyl formamide, benzyl sulfoxide, 4-chlorophenyl sulfone, 4-fluoro-3-nitrophenyl sulfone or mixtures thereof.

29. The composition of claim 27 in which the diluent is a mixture of dimethyl sulfone and N,N-dimethyl formamide.

30. The composition of claim 27 in which the borate ester is trimethanolamine borate, triethanolamine borate, tri(n-propanol)amine borate or mixtures thereof.

31. The composition of claim 27 in which the borate ester is triethanolamine borate.

32. The composition of claim 27 in which the diluent is dimethyl sulfoxide, dimethyl sulfone, N,N-dimethyl formamide or mixtures thereof, and the borate ester is trimethanolamine borate, triethanolamine borate, tri(n-propanol)amine borate or mixtures thereof.

33. The composition of claim 27 in which the diluent is a mixture of dimethyl sulfone and N,N-dimethyl formamide, and the borate ester is triethanolamine borate.

34. The composition of claim 27 in which the organic hydroperoxide is t-butyl hydroperoxide, cumene hydroperoxide, diisopropylbenzene hydroperoxide, 2,5-dimethylhexane-2,5-dihydroperoxide, paramenthane hydroperoxide or mixtures thereof.

35. The composition of claim 27 in which the organic hydroperoxide is cumene hydroperoxide.

36. The composition of claim 27 in which the indicator is benzidine, o-tolidine, 3,3',5,5'-tetramethylbenzidine, 2,7-diaminofluorene, or mixtures thereof.

37. The composition of claim 27 in which the indicator is o-tolidine.

38. A method for determining the presence of a peroxidatively active substance in a test sample, said method comprising contacting said sample with the composition of claim 27, and observing a detectable response.

39. The method of claim 38 in which the diluent is dimethyl sulfoxide, dimethyl sulfone, N,N-dimethyl formamide, benzyl sulfoxide, 4-chlorophenyl sulfone, 4-fluoro-3-nitrophenyl sulfone or mixtures thereof.

40. The method of claim 38 in which the diluent is a mixture of dimethyl sulfone and N,N-dimethyl formamide.

41. The method of claim 38 in which the borate ester is trimethanolamine borate, triethanolamine borate, tri-(n-propanol)amine borate or mixtures thereof.

42. The method of claim 38 in which the borate ester is triethanolamine borate.

43. The method of claim 38 in which the diluent is dimethyl sulfoxide, dimethyl sulfone, N,N-dimethyl formamide or mixtures thereof, and the borate ester is trimethanolamine borate, triethanolamine borate, tri(n-propanol) amine borate or mixtures thereof.

44. The method of claim 38 in which the diluent is a mixture of dimethyl sulfone and N,N-dimethyl formamide, and the borate ester is triethanolamine borate.

45. The method of claim 38 in which the organic hydroperoxide is t-butyl hydroperoxide, cumene hydroperoxide, diisopropylbenzene hydroperoxide, 2,5-dimethylhexane-2,5-dihydroperoxide, paramenthane hydroperoxide or mixtures thereof.

46. The method of claim 38 in which the organic hydroperoxide is cumene hydroperoxide.

47. The method of claim 38 in which the indicator is benzidine, o-tolidine, 3,3',5,5'-tetramethylbenzidine, 2,7-diaminofluorene, or mixtures thereof.

48. The method of claim 38 in which the indicator is o-tolidine.

49. A test composition for determining the presence of a peroxidatively active substance in a test sample, said composition comprising (a) cumene hydroperoxide, (b) an indicator selected from benzidine, o-tolidine, 3,3',5,5'-tetramethylbenzidine, 2,7-diaminofluorene and mixtures thereof, (c) a mixture of dimethyl sulfone and N,N-dimethyl formamide, and (d) triethanolamine borate.

50. A method for determining the presence of a peroxidatively active substance in a test sample said method comprising contacting said sample with the composition of claim 49, and observing a detectable response.

51. A test device for determining the presence of a peroxidatively active substance in a test sample, said device having a carrier matrix incorporated with a test composition comprising
  a. an organic hydroperoxide,
  b. an indicator capable of producing a detectable response in the presence of said hydroperoxide and a peroxidatively active substance,
  c. a diluent having the structure

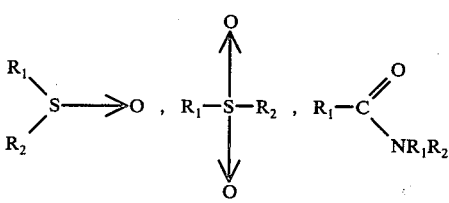

or mixtures thereof, in which $R_1$ and $R_2$, same or different, are hydrogen, alkyl or alkoxy having 1 to about 6 carbon atoms, or aryl, and
  d. a borate ester having the structure

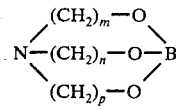

in which $m$, $n$ and $p$, same or different, are integers of 1 to about 4.

52. The test device of claim 51 in which the diluent is dimethyl sulfoxide, dimethyl sulfone, N,N-dimethyl formamide, benzyl sulfoxide, 4-chlorophenyl sulfone, 4-fluoro-3-nitrophenyl sulfone or mixtures thereof.

53. The test device of claim 51 in which the diluent is a mixture of dimethyl sulfone and N,N-dimethyl formamide.

54. The test device of claim 51 in which the borate ester is trimethanolamine borate, triethanolamine borate, tri(n-propanol)amine borate or mixtures thereof.

55. The test device of claim 51 in which the borate ester is triethanolamine borate.

56. The test device of claim 51 in which the diluent is dimethyl sulfoxide, dimethyl sulfone, N,N-dimethyl formamide or mixtures thereof, and the borate ester is trimethanolamine borate, triethanolamine borate, tri(n-propanol)amine borate or mixtures thereof.

57. The test device of claim 51 in which the diluent is a mixture of dimethyl sulfone and N,N-dimethyl formamide, and the borate ester is triethanolamine borate.

58. The test device of claim 51 in which the organic hydroperoxide is t-butyl hydroperoxide, cumene hydroperoxide, diisopropylbenzene hydroperoxide, 2,5-dimethylhexane-2,5-dihydroperoxide, paramenthane hydroperoxide or mixtures thereof.

59. The test device of claim 51 in which the organic hydroperoxide is cumene hydroperoxide.

60. The test device of claim 51 in which the indicator is benzidine, o-tolidine, 3,3',5,5'-tetramethylbenzidine, 2,7-diaminofluorene, or mixtures thereof.

61. The test device of claim 51 in which the indicator is o-tolidine.

62. A test device for determining the presence of a peroxidatively active substance in a test sample, said device having a carrier matrix incorporated with a test composition comprising (a) cumene hydroperoxide, (b) an indicator selected from benzidine, o-tolidine, 3,3',5,5'-tetramethylbenzidine, 2,7-diaminofluorene and mixtures thereof, (c) a mixture of dimethyl sulfone and N,N-dimethyl formamide, and (d) triethanolamine borate.

63. The test device of claim 62 in which said carrier matrix is bibulous paper.

* * * * *